United States Patent
Stuer-Lauridsen

(10) Patent No.: US 10,261,063 B2
(45) Date of Patent: Apr. 16, 2019

(54) METHOD AND SYSTEM FOR MONITORING QUALITY OF BALLAST WATER OF A VESSEL

(71) Applicant: Ballast Water Monitoring A/S, Copenhagen (DK)

(72) Inventor: Frank Stuer-Lauridsen, Holte (DK)

(73) Assignee: Ballast Water Monitoring A/S, Kgs. Lyngby (DK)

( * ) Notice: Subject to any disclaimer, the term of this patent is extended or adjusted under 35 U.S.C. 154(b) by 855 days.

(21) Appl. No.: 14/442,409

(22) PCT Filed: Nov. 14, 2013

(86) PCT No.: PCT/EP2013/073802
§ 371 (c)(1),
(2) Date: May 13, 2015

(87) PCT Pub. No.: WO2014/076171
PCT Pub. Date: May 22, 2014

(65) Prior Publication Data
US 2015/0369787 A1    Dec. 24, 2015

(30) Foreign Application Priority Data

Nov. 14, 2012 (DK) ................................ 2012 70702

(51) Int. Cl.
*G01N 33/18* (2006.01)
*B63J 4/00* (2006.01)
(Continued)

(52) U.S. Cl.
CPC .............. *G01N 33/18* (2013.01); *B63J 4/002* (2013.01); *B63J 99/00* (2013.01); *B63B 2203/00* (2013.01);
(Continued)

(58) Field of Classification Search
CPC .............. C02F 2209/02; C02F 2209/36; C02F 2209/008; C02F 2103/008;
(Continued)

(56) References Cited

U.S. PATENT DOCUMENTS 6,444,119 B1   9/2002   Mains, Jr.
6,823,810 B2   11/2004  Carlson et al.
(Continued)

FOREIGN PATENT DOCUMENTS

SG            185974         12/2012
WO      WO 2005/064560       7/2005
(Continued)

*Primary Examiner* — Mohamed Charioui
*Assistant Examiner* — Jeremy DeLozier
(74) *Attorney, Agent, or Firm* — Peter A. Nieves; Sheehan Phinney Bass & Green PA

(57) ABSTRACT

The present invention relates to a system for monitoring quality of ballast water. The system comprises a central data hub comprising a data hub computer adapted for generating a set of acceptance criteria for ballast water quality parameters at one or more geographic positions based upon uploaded ballast water data from on-board computers of at least two vessels. The uploaded ballast water data indicates where, and possibly when, a volume of ballast water was loaded into a ballast water tank of each of the at least two vessels and the respective values of each of the ballast water quality parameters that are measured on each of the volumes of ballast water. The system for monitoring quality of ballast water further comprises at least two vessels, such as ships, each vessel comprising an on-board ballast water system comprises an on-board computer with a monitor, a data logger, a data storage for storage of a set of acceptance criteria for a number of the ballast water quality parameters corresponding to a geographical position and at least one geographical position. The on-board ballast water system further comprises detection means adapted for logging into (Continued)

the data logger the geographical position where the volume of ballast water is loaded into the ballast water tank and a number of ballast water quality sensors each being adapted for measuring at least one of the ballast water quality parameters of the ballast water in the ballast water piping or in ballast water tank. The on-board ballast water system is further adapted for logging ballast water data comprising a value of each of the ballast water quality parameters into the data logger and the on-board computer being further adapted for downloading the set of acceptance criteria from the central data hub and up-loading the ballast water data and the corresponding geographical position to the central data hub. The on-board computer is adapted to perform a comparison of the values of the ballast water quality parameters with corresponding acceptance criteria corresponding to said geographical position, and to display information on the monitor depending on said comparison.

18 Claims, 6 Drawing Sheets

(51) Int. Cl.
 *B63J 99/00* (2009.01)
 *C02F 103/00* (2006.01)
(52) U.S. Cl.
 CPC ... *B63J 2099/006* (2013.01); *C02F 2103/008* (2013.01); *C02F 2209/008* (2013.01); *C02F 2209/02* (2013.01); *C02F 2209/105* (2013.01); *C02F 2209/36* (2013.01); *Y02A 90/40* (2018.01); *Y02T 70/36* (2013.01)
(58) Field of Classification Search
 CPC .... C02F 2209/105; G01N 33/18; B63J 99/00; B63J 4/002; B63J 2099/006; Y02T 70/36; B63B 2203/00
 See application file for complete search history.

(56) References Cited

U.S. PATENT DOCUMENTS

| | | | |
|---|---|---|---|
| 7,890,226 B2 | 2/2011 | Reynolds et al. | |
| 8,147,673 B2 | 4/2012 | Childers, II et al. | |
| 8,152,989 B2 | 4/2012 | Childers, II et al. | |
| 2003/0176971 A1* | 9/2003 | Daniels | B63J 99/00 702/2 |
| 2004/0129645 A1 | 7/2004 | Perlich et al. | |
| 2005/0016933 A1 | 1/2005 | Perlich et al. | |
| 2005/0155539 A1 | 7/2005 | Randall | |
| 2009/0211507 A1* | 8/2009 | Fielding | B63J 4/002 114/125 |
| 2010/0116647 A1* | 5/2010 | Kornmuller | B63J 4/004 204/228.1 |
| 2011/0120956 A1 | 5/2011 | Ivanter et al. | |

FOREIGN PATENT DOCUMENTS

| | | |
|---|---|---|
| WO | WO 2005/108301 | 11/2005 |
| WO | WO 2009/060813 | 5/2009 |

* cited by examiner

METHOD AND SYSTEM FOR MONITORING QUALITY OF BALLAST WATER OF A VESSEL

FIELD OF THE INVENTION

The present invention relates to a system for monitoring quality of ballast water. The system comprises a central data hub comprising a data hub computer adapted for generating a set of acceptance criteria for ballast water quality parameters at one or more geographic positions based upon uploaded ballast water data from on-board computers of at least two vessels. The uploaded ballast water data indicates where, and possibly when, a volume of ballast water was loaded into a ballast water tank of each of the at least two vessels and the respective values of each of the ballast water quality parameters that are measured on each of the volumes of ballast water. The system for monitoring quality of ballast water further comprises at least two vessels, such as ships, each vessel comprising an on-board ballast water system comprises an on-board computer with a monitor, a data logger, a data storage for storage of a set of acceptance criteria for a number of the ballast water quality parameters corresponding to a geographical position and at least one geographical position. The on-board ballast water system further comprises detection means adapted for logging into the data logger the geographical position where the volume of ballast water is loaded into the ballast water tank and a number of ballast water quality sensors each being adapted for measuring at least one of the ballast water quality parameters of the ballast water in the ballast water piping or in ballast water tank. The on-board ballast water system is further adapted for logging ballast water data comprising a value of each of the ballast water quality parameters into the data logger and the on-board computer being further adapted for downloading the set of acceptance criteria from the central data hub and up-loading the ballast water data and the corresponding geographical position to the central data hub. The on-board computer is adapted to perform a comparison of the values of the ballast water quality parameters with corresponding acceptance criteria corresponding to said geographical position, and to display information on the monitor depending on said comparison.

BACKGROUND OF THE INVENTION

Ballast water is loaded in ports by ships and stabilizes a ship when it is not carrying a cargo. With the ballast water follows native species of aquatic flora and fauna which are discharged with the ship's ballast water into a new environment when the ship loads cargo in a new port. Some of these organisms may survive become invasive and threaten the native ecology around the new port and even spread diseases such as cholera. Local economic activities such as fisheries may be threatened by these activities. Annual losses incurred on economy as a result of the spread of invasive species are staggering and estimated in the EU at more than 30 billion Euros annually. In the U.S. the annual losses are estimated at more than 50 billion USD.

To eliminate or at least minimize the risk of new introductions of invasive species the International Convention for the Control and Management of Ship's Ballast Water and Sediments was adopted in 2004. The Ballast Water Management Convention requires vessels in international traffic to treat their ballast water and meet certain quality criteria before discharging the water. This requirement has fuelled the development of ballast water management systems (BWMS) to allow on-board treatment of the ballast water for the maritime vessels.

However, there remains a need for a system for monitoring the quality of ballast water to ensure compliance with the above-mentioned quality criteria. The system for monitoring the quality of ballast water should preferably allow for safe and energy efficient treatment of the ballast of the vessel.

U.S. patent application No. 2003/0176971 discloses a ballast water monitoring system for tracking the exchange of ballast water in the ballast water tank of a ship. The system comprises an on-board ballast water analysis system, as, which comprises a chemistry probe that may detect the chemical composition of the ballast water contained within the ballast water tank such as its salinity and amount of explosives, illegal drugs, biological agents etc. The ballast water monitoring system furthermore comprises a remote central data management unit (remotely located internet central server) which receives ballast water data and accompanying geographical location information from a plurality of ships. The central server is used to organize and disseminate the chemistry tracking data collected from a large number of ships. The central server may be coupled to the on-board ballast water analysis system through the Internet, or wirelessly via a cellular or satellite telephone modem. The governmental authorities can verify that the exchange of ballast water takes place outside the 200 nautical miles Exclusive Economic Zone, as regulations state. In the preferred embodiment of the invention, the salt content of ballast water is detected and when a change in salt content of the ballast water exceeds a pre-determined threshold, the geographic location of the ship is determined for example by GPS. A set of data representing this information is transmitted to the remotely located internet central server.

U.S. Pat. No. 7,890,226 discloses an emission management system for a vessel. The emission management system includes a monitoring assembly for monitoring an emission from the vessel. The monitoring assembly is adapted to automatically detect the emission from the vessel and generate a data set representative of a vessel location at a time the emission occurred. The emission management system also includes a data storage system in communication with the monitoring assembly for recording the data set generated by the monitoring assembly. In one embodiment the emission management system is adapted to treat and monitor the ballast water of the vessel. The emission management system may comprise a treatment device and emission sensor which is adapted to determine the concentration or quantity of contaminants in the treated ballast water.

U.S. 2005/0016933 discloses apparatuses and methods of a ballast water treatment system for a vessel. The ballast water treatment system includes a control system and a ballast tank system. The control system controls a concentration of a biocide in the ballast tank system. The control system is capable of controlling the concentration of a biocide in the ballast tank system by controlling the amount of the biocide feed into the ballast tank system from the biocide generation system. Parameters of the control system, such as the concentration of residual biocide, can be set by the user to treat different types of ballast water differently and/or comply with local, state, federal, and/or international regulations.

SUMMARY OF THE INVENTION

A first aspect of the invention relates to a system for monitoring quality of ballast water comprising:

a central data hub comprising a data hub computer adapted for generating a set of acceptance criteria for ballast water quality parameters at one or more geographic positions based upon uploaded ballast water data from on-board computers of at least two vessels; wherein the uploaded ballast water data indicates where, and possibly when, a volume of ballast water was loaded into a ballast water tank of each of the at least two vessels and the respective values of each of the ballast water quality parameters that are measured on each of the volumes of ballast water;

and the at least two vessels, such as at least two ships, that each comprises an on-board ballast water system comprising:

an on-board computer with a monitor, a data logger, a data storage for storage of a set of acceptance criteria for a number of the ballast water quality parameters corresponding to a geographical position and at least one geographical position detection means adapted for logging into the data logger the geographical position where the volume of ballast water is loaded into the ballast water tank, a number of ballast water quality sensors each being adapted for measuring at least one of the ballast water quality parameter of the ballast water in the ballast water piping or in ballast water tank, and adapted for logging ballast water data comprising a value of each of the ballast water quality parameters into the data logger, the on-board computer being further adapted for downloading the set of acceptance criteria from the central data hub and up-loading the ballast water data and the corresponding geographical position to the central data hub, wherein the on-board computer is adapted to perform a comparison of the values of the ballast water quality parameters with corresponding acceptance criteria corresponding to said geographical position, and to display information on the monitor depending on said comparison.

If the one or more values of the ballast water quality parameters fail(s) to comply with the corresponding acceptance criterion/criteria, the loaded volume of ballast water may be discharged. A suitable message about the non-compliance of the ballast water may be displayed on the monitor of the on-board ballast water system to inform an operator of the non-acceptance of the ballast water. Alternatively to discharging the volume of ballast water from the vessel, the loaded volume of ballast water may be subjected to a disinfection treatment or a supplemental treatment, if an earlier treatment already has been carried out, in an effort to reduce the and reach compliance with the set of acceptance criteria.

The skilled person will understand that each of the on-board computers may be configured to acquire and store other types of relevant environmental information in relation to the loading of ballast water from the central data hub such as meteorological data, maritime traffic data etc.

Each of the on-board ballast water systems may comprise a clock device adapted for logging a time of the year and/or time of the day into the data logger indicating when the volume of ballast water was loaded into the ballast water tank. This can be effected through the use of a timed geographical positioning system such as a system comprising a GPS receiver. The on-board computer may comprise or have access to the geographical position, e.g. expressed in terms of GPS coordinates, and time data generated by such a GPS receiver. Hence, the geographical position of vessel and the time where the volume of ballast water was loaded into the ballast water tank may be logged by the data logger of the on-board computer.

The information displayed on the monitor depending on the comparison of the values of the ballast water quality parameters and the corresponding acceptance criteria preferably comprises an acceptance or non-acceptance of the quality of the ballast water loaded into the ballast water tank.

Furthermore, each of the on-board computers is preferably adapted for wireless downloading of a second set of acceptance criteria, corresponding to the same geographical position as the set of acceptance criteria, and to replace the set of acceptance criteria with the second set of acceptance criteria. This embodiment allows the acceptance criteria to be updated regularly and/or automatically by the data hub computer at the central data hub as additional information about appropriate acceptance criteria becomes available through analysis of the uploaded ballast water data from on-board computers of the at least two vessels. The skilled person will understand that the present system for monitoring the quality of ballast water preferably comprises more than two vessels for example more than 10 or 20 or 50 vessels. This will increase the amount of uploaded ballast water data and may accordingly speed-up the learning process of analysis software or applications running on the data hub computer The ballast water quality sensors are preferably adapted for measuring one or more ballast water quality parameters from a group of {phytoplankton population, zooplankton population, bacterial population, particle size distribution}. Various types of measurement technologies may be utilized for measuring these ballast water quality parameters. The measurement technology preferably comprises at least one of {fluorescence, light scattering, Near Infrared (NIR)}.

According to preferred embodiment of the system, the ballast water quality sensors are adapted for measuring one or more additional ballast water quality parameters to those mentioned above and include these in the ballast water data transmitted to the central data hub. These additional ballast water quality parameter(s) are preferably selected from a group of {salinity, temperature, transmittance}. Values of the additional ballast water quality parameters may alternatively be provided by pre-existing ballast water sensors of the vessel for example sensors that are part of an existing or installed ballast water treatment system.

According to an advantageous embodiment of the invention, the data hub computer is adapted for generating the set of acceptance criteria for the ballast water quality parameters based on environmental data collected at the geographic position of the vessel in addition to the measured values of the ballast water quality parameters. These environmental data are accordingly supplemental to the measured ballast water quality parameters. The environmental data may comprise metrological data such as weather conditions, ambient air and water temperature, rain, sun etc. that are collected by either appropriate on-board sensors or remotely via e.g. a weather satellite. The environmental data may comprise tidal data at the geographic position of the vessel in question. These environmental data may be important in assessing the quality of the loaded ballast water and may indicate causality correlations between certain measured ballast water quality parameters and specific environmental conditions. These correlations may be recognized by an algorithmic enhancement process applied to the uploaded ballast water data by the data hub computer and exploited in the generation of the set of acceptance criteria for the ballast water quality parameters. As time evolves the on-going uploading of respective ballast water data to the central data hub of the system from the plurality of vessels at various geographic positions will increase the size of the available pool of ballast water data and thereby allow the algorithmic enhancement process to recognize specific patterns in the pool of ballast water. The specific patterns in the pool of ballast water may be used by the algorithmic enhancement process to adjusting an individual acceptance criterion, or adjusting several individual acceptance criteria, of the set of acceptance criteria accordingly. Furthermore, the new parameters may be added to an individual existing acceptance criterion. Hence, the set of acceptance criteria may be updated from time to time reflecting an on-going learning process of the algorithmic enhancement process to provide more reliable settings of the acceptance criteria.

Another advantageous embodiment of the present system comprises two or more ballast water quality sensors adapted for measuring the values of the same ballast water quality parameter. The on-board computer of each vessel is adapted for calculating a difference between the values of a specific ballast water quality parameter measured by the two or more different ballast water quality sensors and to compare the calculated difference with an acceptance criterion. The system may display information on the monitor depending on said comparison. The use of the two or more different ballast water quality sensors may in the alternative be accomplished by arranging the on-board ballast water system such that the same ballast water quality sensor is configured for analyzing ballast water samples from more than a single location of the ballast water tank and piping and thereafter performing the above mentioned calculation. This embodiment is well-suited for so-called indicative assessment of the ballast water quality parameter or parameters in question where difference between the values of the specific ballast water quality parameter is derived from measured values before and after ballast water treatment. This leads to a number of advantages in connection with treatment of ballast water as explained below in further detail in connection with the drawings In a further preferred embodiment, the on-board ballast water system of each vessel comprises at least one ballast water treatment device. The at least one ballast water treatment device being adapted for treating the ballast water of the ballast water monitoring system in at least two different operating modes. The on-board computer is adapted for regulating or switching the ballast water treatment device between the different operating modes depending on said comparison between the values of the ballast water quality parameters and the corresponding acceptance criteria. Each of the ballast water treatment devices may comprise an inlet and an outlet pipe adapted for leading the ballast water to and from the ballast water treatment device, respectively. A first of the two different ballast water quality sensors, adapted for measuring the same ballast water quality parameter, is arranged in connection with the inlet pipe and a second ballast water quality sensor, adapted for measuring the same ballast water quality parameter, is arranged in connection with the outlet pipe. In this manner, the first and second ballast water quality sensors are measuring the ballast water entering and leaving, respectively, the ballast water treatment device, i.e. before and after the treatment process.

The at least one ballast water treatment device may be configured to filter the ballast water or apply one of UV-treatment, hydrocyclone and chlorination processes to the ballast water.

According yet another embodiment of the present system for monitoring quality of ballast water, the on-board ballast water system of each vessel comprises a ballast water quality sensor adapted for measuring a ballast water quality parameter. In this embodiment, the ballast water piping system may be arranged for exposing the ballast water quality sensor to the ballast water at two different positions of the ballast water piping system and the on-board computer adapted for calculating the difference between values of a specific ballast water quality parameter measured by said ballast water quality sensor at the two different positions and to compare the calculated difference with an acceptance criteria and to display information on the monitor depending on said comparison.

The on-board computer of each vessel may in principle be configured for uploading the ballast water data to the central data hub by a wired or wireless data communication link. The use of the wired data communication link may however be disadvantageous in certain systems as the uploading of the ballast water data is limited to situations where the vessel is located in a port or harbour with access to a suitable data communication interface. The wireless data communication link will typically allow a faster and more flexible uploading of the ballast water data. The wireless data communication link may for example comprise a satellite link that may transmit the ballast water data over a suitable communication channel according to a suitable data communication protocol such as TCP/IP.

A second aspect of the invention relates to an on-board ballast water system for a vessel, comprising:

an on-board computer with a monitor, a data logger, a data storage for storage of a set of acceptance criteria for a number of ballast water quality parameters corresponding to a geographical position, at least one geographical position detection means adapted for logging into the data logger the geographical position where the volume of ballast water is loaded into the ballast water tank, a number of ballast water quality sensors each being adapted for measuring at least one of the ballast water quality parameter of the ballast water in the ballast water piping or in ballast water tank, and adapted for logging ballast water data comprising a value of each of the ballast water quality parameters into the data logger.

Furthermore, the on-board computer is adapted to perform a comparison of the values of the ballast water quality parameters with corresponding acceptance criteria corresponding to said geographical position. The on-board computer displays information on the monitor depending on said comparison and the on-board computer is adapted for downloading of the set of acceptance criteria from a central data hub.

A third aspect of the invention relates to a method of monitoring quality of ballast water in a ballast water tank or ballast water piping on-board a vessel, such as a ship, comprising steps of:

recording or entering into a data logger a geographic position where a volume of ballast water was loaded into the ballast water tank; measuring respective values of one or more ballast water quality parameters of the loaded volume of ballast water;

logging the respective measured values of the ballast water quality parameters into the data logger;

downloading a set of acceptance criteria corresponding to the geographic position where the volume of ballast water loaded from an central data hub and into an on-board computer equipped with a monitor;

comparing the values of the measured ballast water quality parameters in the data logger with the corresponding acceptance criteria;

displaying information on the monitor depending on said comparison.

The method of monitoring the quality of the ballast water may comprise:

keeping in the volume of loaded ballast water in the ballast water tank or discharging the volume of loaded ballast water from the ballast water tank at the geographic position or area depending on said comparison. Hence, if the value of each of the measured ballast water quality parameters complies with the corresponding acceptance criterion or criteria, the loaded volume of ballast water has an acceptable quality. In the opposite situation, the loaded volume of ballast water has an unacceptable quality and may be discharged or subjected to treatment with the above-described at least one ballast water treatment device and the ballast water quality parameters measured again in this connection.

According to another embodiment, the volume of ballast water may be treated during ballasting to reduce content of contaminants e.g. native species of aquatic flora and fauna in the volume ballast water. This embodiment may comprise further steps of:

measuring values of the same ballast water quality parameter during ballasting before and after the ballast water treatment, calculating a difference between the values of the same ballast water quality parameter, comparing the calculated difference between the same ballast water quality parameter with an acceptance criteria and display information on the monitor of the on-board computer depending on said comparison.

BRIEF DESCRIPTION OF THE DRAWINGS

Various embodiments of the present invention as well as additional objects, features and advantages of the invention will be described in more detail in the following illustrative and non-limiting description of embodiments of the invention with reference to the appended drawings, wherein.

DETAILED DESCRIPTION OF PREFERRED EMBODIMENTS

Figure 1:
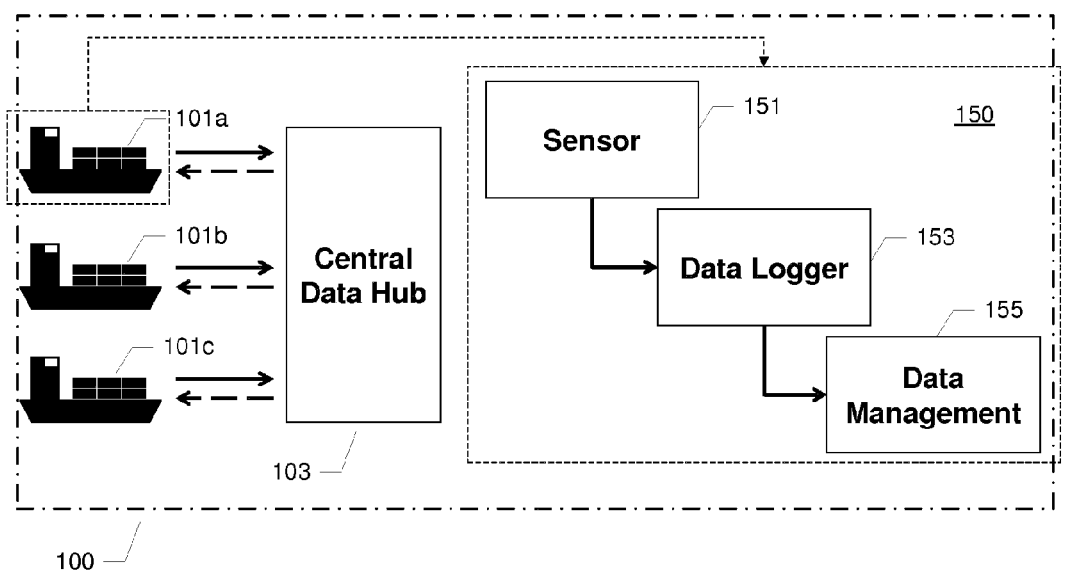
FIG. 1 is a schematic illustration of the architecture of a system for monitoring the quality of ballast water (BWMS) according to a first embodiment of the invention.

FIG. 1 is a schematic illustration of the architecture of a system 100 for monitoring the quality of ballast water (BWMS) according to a first embodiment of the invention. An on-board ballast water system 150 on each vessel of a plurality of vessels 101a, 101b, 101c may be fully or partly integrated with an existing ballast water management/treatment system of the vessel in question. The BWMS 100 comprises a central data hub 103 as illustrated. This central data hub 103 is preferably stationary and located on land or alternatively on-board a vessel. The central data hub 103 comprises a data hub computer (not shown) adapted for generating a set of acceptance criteria for ballast water quality parameters at one or more geographic positions or under similar environmental conditions in other geographic positions based upon uploaded ballast water data at the one or more geographic positions from on-board computers (not shown) of a plurality of vessels of the BWMS. The uploaded ballast water data indicates where, and preferably when, a volume of ballast water was loaded into the ballast water tank of each of the plurality of vessels or ships 101a, 101b, 101c and the values of each of the ballast water quality parameters that are measured on each of the volumes of ballast water. The ballast water system of each of the vessels is configured for monitoring and logging a plurality of values of respective ballast water quality parameters related to discharge quality criteria for the volume of ballast water at a number of sampling locations in the on-board ballast water system on loading, during treatment and discharge of the volume of ballast water. Data such as the ballast water data collected by the on-board ballast water system are stored in a data storage associated with a data logger 153. The ballast water data are analysed in the on-board computer or other data management facility 155 on board the vessel. The ballast water data may also include various optional, but often helpful, ballast water quality parameters such as temperature and salinity of the loaded ballast water and certain vessel specific environmental data like geographical position data and tidal data. These ballast water data are collected and structured in a preferred format by the on-board computer of the vessel and transmitted via a suitable wireless bi-directional data communication link to the central data hub 103. The central data hub 103 of the present BWMS is configured to combine and analyse the respective ballast water data from many ballasting operations of the plurality of vessels 101a, 101b, 101c to improve performance of the BWMS 100 as explained below in additional detail in the section on the operation of the central data hub 103.

The on-board ballast water system 150 of each vessel may be initially set to react at pre-set indicator points or initial set of acceptance criteria for the ballast water quality parameters and provide an alarm for an operator of the on-board ballast water system if a measured value of a ballast water quality parameter is fails to comply with the corresponding preset acceptance criterion of the set of acceptance criteria. The preset acceptance criterion may for example comprise a threshold value or a preset range for the ballast water quality parameter in question. These acceptance criteria of the on-board ballast water system 150 can be serviced and the acceptance criteria may be adjusted remotely by transmission of an updated set of acceptance criteria from the central data hub 103. The updated set of acceptance criteria is loaded into the data storage of the on-board ballast water system 150 to replace or supplement the initial set of acceptance criteria. The ballast water data collected by the on-board ballast water system is transferred to the central data hub 103 as previously described to be analysed and correlated with optional environmental or external data that are specific to the geographic position of the ship for example meteorological data and data on chlorophyll, nutrient levels, turbidity etc. The ballast water data from the plurality of vessels for each type of BWMS are combined by the data hub computer (not shown) with optional external data. The data hub computer determines certain patterns of system performance using a machine learning approach to improve performance of each of the on-board ballast water systems 150 by generating and transmitting an updated set of acceptance criteria associated with the relevant ballast water quality parameters to each of the on-board ballast water systems.

Each of the on-board ballast water systems 150 comprises a number of ballast water quality sensors 151 measuring selected ballast water quality parameters, i.e. these may be both criteria for which ballast water discharge standards exist and various optional ballast water quality parameters. The on-board ballast water system 150 further comprises a data logging device 153, a PC based data analyser with a monitor or display unit (not shown) and a data management module 155 which preferably comprises the data communication interface for transfer or transmission of the ballast water data to the central data hub 103. The data communication interface is also used for downloading the set of acceptance criteria from the data hub 103 as schematically illustrated by the pair of arrows between each of the vessels 101a, 101b, 101c and the central data hob 103. A pump and sampling equipment may be included in the on-board ballast water system for ballast water sampling purposes. The system 150 is preferably permanently installed on-board the vessels 101a, 101b, 101c. Ballast water samples are preferably collected or drawn from the ballast water system of the ship at a number of sampling points providing in-line samples from the ballast water system. The ballast water samples are preferably taken from a ballast water piping or the ballast water tank of the vessel. The sampling of ballast water at several points may be achieved through continuously flushed sampling loops or by several monitoring devices. A pump, sampling equipment and the necessary ballast water piping is included for ballast water sampling purposes. The ballast water sampling may be conducted as isokinetic sampling but that is not a requirement if other means of representativeness assessment of the volume of ballast water is available.

Figure 2:
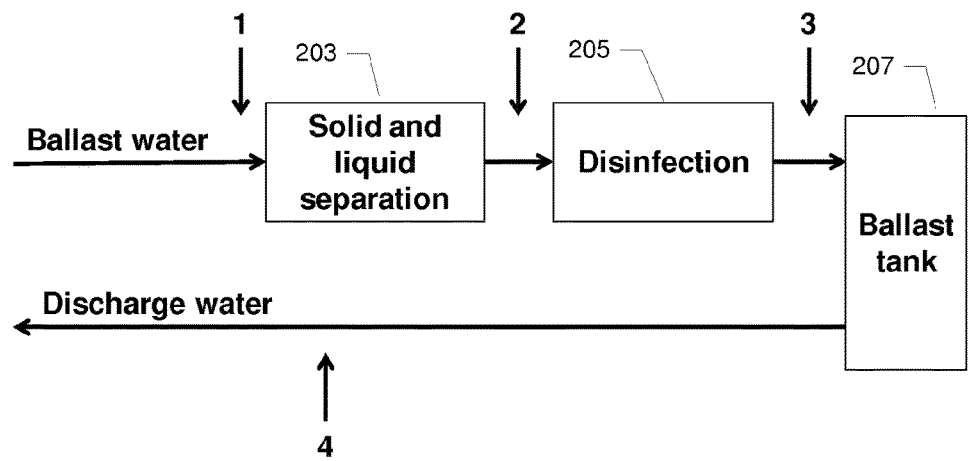
FIG. 2 is a flowchart showing ballast water treatment and monitoring steps of the BWMS according to the first embodiment of the present invention.
Figure 3:
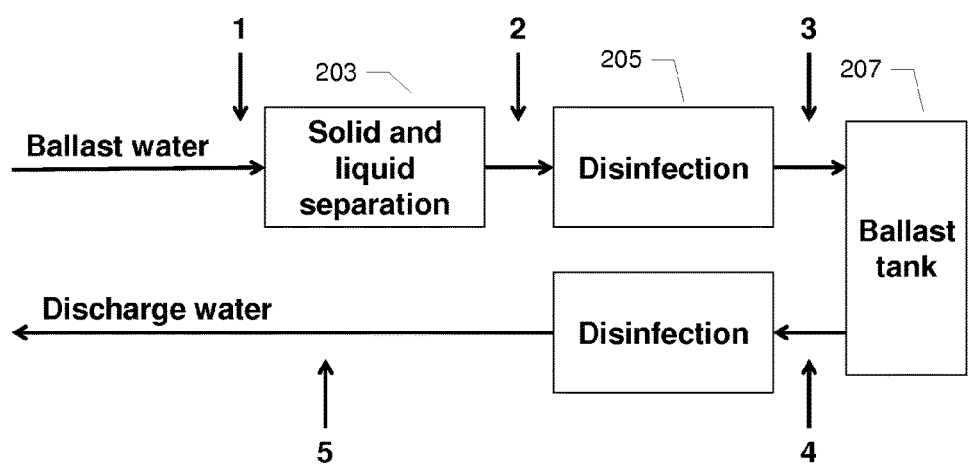
FIG. 3 is a flowchart showing ballast water treatment and monitoring steps of the BWMS according to a second embodiment of the present invention.

As schematically illustrated on FIGS. 2 and 3, the measurement or sampling of the ballast water quality parameters may take place by the previously discussed ballast water quality sensors 1, 2, 3, 4 and 5 positioned in the ballast water piping or via a piping arrangement leading a side stream from the sampling point through to a particular ballast water quality sensor. The ballast water streams from several to all of the sampling/measurement points may converge in one sensor continuously flowing from sampling points through a multivalve into the ballast water quality sensor and back to the main ballast water stream. As schematically illustrated, the measurement of the value of each of ballast water quality parameters may take place before and/or after each of several ballast water treatment devices 203, 205. One of the ballast water treatment devices 203, 205 may be adapted for separating solids and liquids, e.g. a particle filter or a device adapted for disinfecting the ballast water before a volume of ballast water is loaded into a ballast water tank 207. In the latter case this can be carried out at ballast water loading/uptake or at ballast water discharge. The sequencing of the ballast water sampling is preferably tied to the flow rate of the ballast water to ensure sampling of comparable ballast water. The optional sampling of ballast water at discharge (i.e. at sensor position 4) is tied to a flow regime where the ballast water treatment system applies disinfection on discharge. In that case sampling points 2, 4 and 5 are preferably used.

Position of Sensor and Additional Monitoring On Board

Ballast water quality sensors for measurement of values of ballast water quality parameters such as one or more of phytoplankton population, zooplankton population, bacterial population and particle size distribution are positioned to allow for a defined subsample of ballast water of the main stream to be monitored. Additional monitoring and measurement of environmentally oriented and optional quality parameters may include e.g. salinity, temperature, transmittance or absorbance, turbidity, total organic carbon and total suspended solids. These may be measured by ballast water quality sensors of the on-board ballast water system or collected as part of the ballast water management system's existing performance measurement and monitoring programme including e.g. energy consumption, filter back pressures and wash intervals, data for Total Residual Oxidant (TRO) and Oxidation-Reduction Potential (ORP). This patent specification does not describe details of the ballast water quality sensors which must deliver the ballast water quality parameter values as these may be sensors that are well-known to the skilled person. The ballast water quality sensors may measure particle density and/or size and a viability measurement, e.g. monitoring of chlorophyll a, staining with fluorescein, monitoring of tryptophan. The sensors for particles and viability of organisms that collect data to a local data logger are positioned to allow for a well-defined subsample of main stream of ballast water to be monitored.

Optional ballast water data may be collected as part of the vessel's existing performance monitoring and may include the ship's geographic position, energy generation, fuel consumption, speed and other general descriptors of the vessel.

Figure 4:
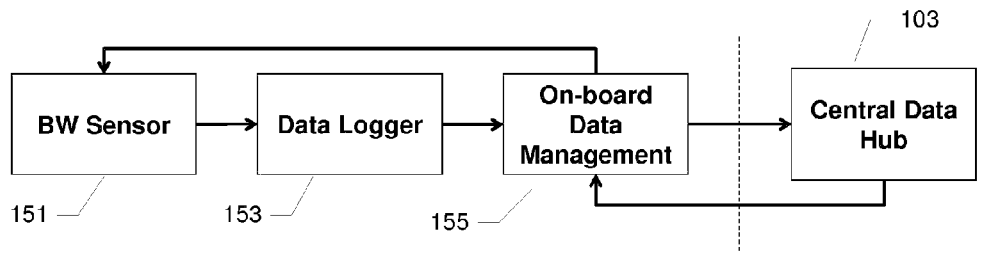
FIG. 4 is a simplified flowchart of an overall data flow in a BWMS according to the first and second embodiments of the invention.

FIG. 4 is a simplified flowchart of the overall data flow between the central data hub 103 and the ballast water system 150 of each of the vessels of the BWMS 100.

Data Collected From Other Sources

The collected ballast water data from each vessel in connection with ballasting or de-ballasting, i.e. the uptake or loading of ballast water or discharge of ballast water, are transferred to the central data hub for analysis and correlation with the external data from other sources such as environmental data associated with the geographic position of the vessel. The external or environmental data related to the ballasting or de-ballasting may be meteorological data or remotely acquired data on ambient water conditions of the vessel such as chlorophyll levels, nutrient levels, turbidity etc. The ballast water data delivered by each of the on-board ballast water systems of the present BWMS are combined and patterns of system performance using machine learning approach are used to improve the local or on-board system's performance as previously discussed. The central data hub preferably comprises a data hub computer capable of handling large data sets.

The preferred automatic operation of the on-board ballast water systems acquires the ballast water data on board each of the vessels, determines the relevant or desired ballast water quality parameters and provides performance information to the vessel in real time. The on-board ballast water system also transfers the measured ballast water data to be analysed together with the environmental data and optional data to provide a feedback to the on-board ballast water system. There are at least two options for feedback mechanisms:

1) Local feedback based on ballast water data of the on-board ballast water system and generated on-board;

2) Shared feedback in form of updated acceptance criteria computed by the hub computer on the basis of ballast water data of similar systems in the plurality of vessels of the BWMS.

Both feedback mechanisms may be operating simultaneously and may over time influence the settings of the set of acceptance criteria through machine learning.

The values of the ballast water quality parameters measured by the ballast water quality sensors 151 are logged by the data logger 153 to the on-board data storage of the on-board ballast water system 150. The on-board computer has access to these values. The on-board computer comprises a suitable application program that allows the operator to retrieve the originally collected values of the ballast water quality parameters for inspections on board the vessel. The ballast water quality parameters from the ballast water quality sensors may include particle and viability data of the volume of ballast water and additional ballast water sensor data such as salinity and transmittance. Environmental data may comprise other information collected from the vessel's repository e.g. geographic position of the vessel at the loading of the volume of ballast water (e.g. expressed in GPS coordinates), vessel speed, vessel stability and list, ballast system operational data etc. as mentioned above. The primary logged on-board ballast water quality parameters are preferably analysed for compliance with the current set of acceptance criteria to be set by the manufacturer of the BWMS or possibly by the IMO D-2 requirement. These data are presented to the system operators and other personnel on-board the vessel together with the relevant acceptance or non-acceptance indications or messages. The relevant acceptance or non-acceptance indications or messages are preferably presented on the monitor of the on-board ballast water system.

Upon operating and monitoring the on-board ballast water system repeatedly, the previously discussed ballast water data, possibly comprising the optional ballast water parameters, and the associated or related environmental data are analysed by an algorithmic enhancement process executed on the data hub computer. The data hub computer provides feedback for changing and optimizing the preset set of acceptance criteria. In vessels of the BWMS with a trading pattern frequently including the same limited number of ports (i.e. geographic positions), such as ro-ros and container feeders, a data repository of ballast water treatment performance is relatively rapidly constructed in the algorithmic enhancement process of the data hub computer as described in further detail below. Accumulated ballast water data from all of the plurality of vessels encompassed in the present BWMS are then combined and fed to the central algorithmic enhancement process. The algorithmic enhancement process may include certain algorithms developed for machine learning purposes for central and local data management facilities. The ballast water data from an individual on-board ballast water system may also be combined with the data bank from similar systems, e.g. in the same fleet or from the same manufacturer, to provide a large pool of ballast water data to develop ballast water performance patterns. These may not necessarily be related to geographical position but instead to combinations of key parameters recognised by their interdepending pattern, and the central data hub 103 may transmit feedback in form of updated sets of acceptance criteria to the on-board ballast water systems and/or its operators Underlying Database of BWMS (Filter Components)

The overall system may include information on basic characteristics of each of the BWMS if more than one is used. This option is preferably not available to the operator(s) but preferably set by the BWMS manufacturer. The display of performance for the BWMS ('Evaluation of input parameters against database') is part the information (FIG. 10) provided to the operator in a data log. The data collected for particles may be e.g. size class distribution and/or average density.

---

Box 1. Example of underlying database of BWMS shown with exemplary brand names.

1. The applied type of treatment technology of the BWMS is selected from a dropdown menu (FIG. 10) in the spread sheet and the underlying database identifies the current filter type used for the chosen application.

2. The measured particle size distribution data is compiled into the two size ranges 10-50 μm and >50 μm and concentration is calculated.

| In situ measurements | |
|---|---|
| Particle concentration > 50 μm/m$^3$ | Particle concentration 10 < x < 50/mL |
| 800 | 6000 |

3. The number of particles, which can be expected at applied filter efficiency at maximum load, are listed and compared to the calculated particle concentrations. Results are given as whether the particle concentrations are within the maximum limit of expected value or not.

| Evaluation of input parameters against database | | |
|---|---|---|
| Filter type | Max number of particles > 50 μm | Above expect value for > 50 um |
| Bollfilter | 1000 | NO |
| | Max number of particles 10 ≤ x ≤ 50 | Above expected value for 10 < x < 50 |
| | 500 | YES |

4. Deviations are calculated by comparing measured and maximum particle values and are published as factors, thus positive values will mean exceeding the filter specs and negative values that value are within the expected range. The values are not referring to D-2 standards - only to expected filter performance.

| Evaluation of input parameters against database | |
|---|---|
| Display > 50 | Deviation from expected |
| Filter not performing to standard | -10% |
| Display 10 < x < 50 | Deviation from expected |
| Filter performing to standard | -20% |

---

Example With Particle and Viability Monitoring and Local Data Assessment

Figure 5:
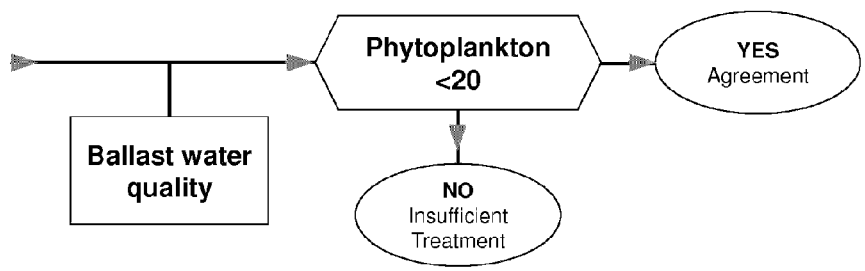
FIG. 5 shows a comparison between an acceptance criterion associated with the specific ballast water quality parameter fluorescence photosynthetic activity in a volume of ballast water.

During a test of an experimental BMWS a ballast water quality sensor or device based on detection of in-situ fluorescence of chlorophyll a from live organisms (photosystem II) was utilized. The vast majority of photosynthetic activity in a ballast water sample is related to a size fraction between 10 and 50 μm. Compliance with the D-2 requirement would require estimation when less than 10 viable phytoplankton per mL is encountered; Due to the detection limits of the ballast water quality sensor in question a higher semi-quantitative limit of 20 viable phytoplankton is used for the basic decision tree and the algorithm for determining indication of BWMS performance. FIG. 5 shows a comparison between an acceptance criterion associated with the specific ballast water quality parameter fluorescence photosynthetic activity in the volume of ballast water.

The algorithmic enhancement process executed on the data hub computer for indicative assessment of the ballast water quality parameter phytoplankton population of the tested ballast water sample is based on three resulting variables given by a fluorescence ballast water quality sensor; the biomass (f0) and viability (fv/fm). f0>20 ∧ fv/fm>0.3 ⇒ number of viable phytoplankton per mL>20.

---

Box 2. Example of calculation of the viable number of phytoplankton.

---

The ballast water samples are measured with a fluorescence sensor resulting in biomass (f0) and viability (fv/fm) output.

| In situ measurements | | |
|---|---|---|
| Sample | Biomass (f0) | Viability (fv/fm) |
| 1 | 250 | 0.538 |

The output is assessed by applying the indicative assessment criteria:
When f0 > 20 ∧ fv/fm > 0.3 ⇒ number of phytoplankton > 20

Indication of viable phytoplankton

| Sample | Assessment | Result shown in display | Data transfer |
|---|---|---|---|
| 1 | f0: 250 > 20 fv/fm: 0.538 > 0.3 | Viable organisms detected above limit | Quantitative |

---

The fluorescence parameter value is preferably combined with determination of particle size distribution. When all particles are considered of biological origin the particle concentrations acts as an enumeration of the maximum possible number of organisms in the respective size categories. This is a conservative position in certain waterways, but may be amended by turbidity measurements. In connection with ballast water discharge measurements this is less of a problem since the bulk of suspended inorganic particles will settle over time leaving the less dense biological material in the water column.

For a clear indication that the on-board ballast water treatment system fails to operate according to the desired acceptance criteria an exceedance of 10 times the D-2 regulation is used (>100 viable organisms). Respective values of the fluorescence measurements and viable phytoplankton values indicate that in order to have more than 100 organisms/mL of the product of f0 and fv/fm must have a value 75. This assumption applies for measurements where f0>20 and fv/fm is above 0.300. The basic decision tree of the combined fluorescence and particle size distribution measurement can be seen in FIG. 6 where an exemplary algorithm is presented. When the two measurement techniques are combined a more rugged indication analysis to establish a clear D-2 exceedance of phytoplankton is obtained.

Figure 6:
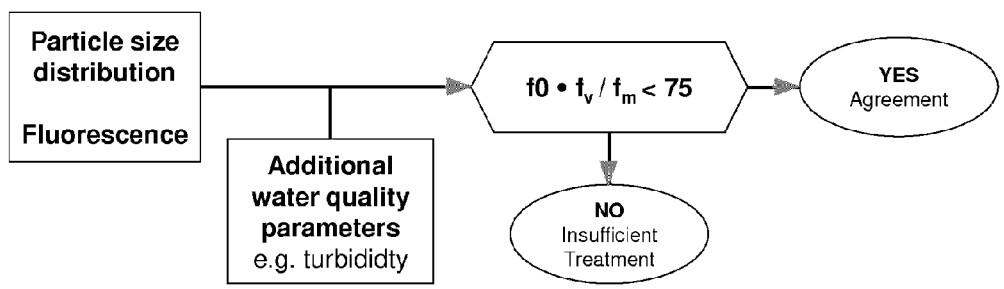
FIG. 6 shows a comparison between one or more acceptance criteria associated with respective ballast water quality parameters such as fluorescence photosynthetic activity etc. in a volume of ballast water.

FIG. 6 shows the decision tree for combined particle size distribution and fluorescent measurement. f0 is bulk biomass and fv/fm is viability.

---

Box 3. Determination of phytoplankton population via fluorescence value and particle size distribution measurements combined.

---

The product of the fluorescence measurement output f0 and fv/fm is calculated and compared to the number of particles measured (in the size category 10-50 μm) above the maximum expected. When the product of fluorescence values are larger than 75 and the number of particles exceeding the expected value are above 100, it is assumed that there is above 100 viable phytoplankton per mL in the sample of ballast water.

Assessment of fluorescence and particle size and distribution results

| No. of particles above expected (10-50 μm) | f0 * fv/fm | f0 * fv/fm > 75 | Deviation (>75) | Display |
|---|---|---|---|---|
| 1000 | 134.5 | YES | 34.5% | Above 100 viable phytoplankton/ mL |

---

In this case the operator(s) of the BWMS are preferably warned by a suitable message on the monitor that system performance is substandard. Hence, continued operation of the BWMS may be indicative of non-compliance with the relevant quality standard when the earlier loaded ballast water is discharged.

Example With Particle and Viability Monitoring and Central Data Assessment

The monitoring of particles in BWMS with filters as outlined above and the data pattern in the measured size distribution intervals is carried to the data repository. The viability response in the same intervals or the sum of the intervals is carried along as well. In this case the dataset is characterised by the two primary data on particles in the sample of ballast water—the density (N) and the viability (V).

---

Box 4. Example of a basic algorithm component for particle and viability data.

---

The basic algorithm has the following structure:

f(size < 10) = N1; V1 + N7; V7 + N13; V13

Σf(size 10-<50) = f(size 10-<20) + ... + f(40-<50) = (N2; V2 + N8; V8 + N14; V14) + ... + (N5; V5 + N11; V11 + N17; V17)

f(size > 50) = N6; V6 + N12; V12 + N18; V18

Except when in summation mode (Σ of size classes) the plus sign does not signify a mathematical addition, but rather a database attachment to a specific dataset. The data on particles and viability are grouped and denoted as shown in the table below.

| Density of particles | | Viability measure | | |
|---|---|---|---|---|
| Major size ranges | Minor size ranges | e.g. Chlorophyl | e.g. NaDPH | Other |
| f(size < 10) | f(size < 10) | N1; V1 | N7; V7 | N13; V13 |
| Σf(size 10-<50) | f(size 10-<20) | N2; V2 | N8; V8 | N14; V14 |
| | f(size 20-<30) | N3; V3 | N9; V9 | N15; V15 |
| | f(size 30-<40) | N4; V4 | N10; V10 | N16; V16 |
| | f(size 40-<50) | N5; V5 | N11; V11 | N17; V17 |
| f(size > 50) | | N6; V6 | N12; V12 | N18; V18 |

---

The data (Ni) may be coupled with a number of ballast water quality parameters and additional environmental data (for illustrative purposes only: they will be forming i number of columns to the right in the table). The ballast water quality parameters may comprise the previously discussed optional parameters like salinity, temperature, transmittance or absorbance, turbidity, total organic carbon and total suspended solids. All on-board recorded ballast water data are collected for the purpose of building a correlation database in the central data hub 103 computer.

BWMS Operation Adjusted to Prior Performance Information

As described above, the ballast water data related to the individual on-board ballast water systems may be used for the updating or adjusting the set of acceptance criteria and possibly alarm levels. As an example, a frequent poor performance of chlorophyll of a UV unit of the ballast water treatment system in the same port (geographic position) at high turbidity and good performance at low turbidity is recognized the on-board ballast water system—please refer to Box 3. The on-board ballast water system is configured to warn the on-board operators to manually ensure lower turbidity by a simple management procedure (e.g. using alternative sea chest), to manually or automated ensure improved ballast water treatment characteristics (e.g. by lowering pump rate or increasing UV lamp intensity).

---

Box 5. Increasing BWMS treatment efficacy from algorithm enhancement process of the data hub computer.

---

Chlorophyll performance algorithm show poor performance:
f0 * fv/fm > 75
BWMS technology efficacy data (from literature or operator, e.g. for UV technology):
Actual Treatment Dose = Approved Treatment Dose (from Manufacture's Type Approval, typically 140-560 mJ/cm2) * 1/ Turbidity (transmittance)

Approved Treatment Dose * Actual Flow rate/Approved Flow rate = Actual Treatment Dose
In example (unit less): 75 = 560 * 1/0.2 (Turbidity) * pump rateActual/pump rateApproved

---

Central Data Hub

Figure 7:
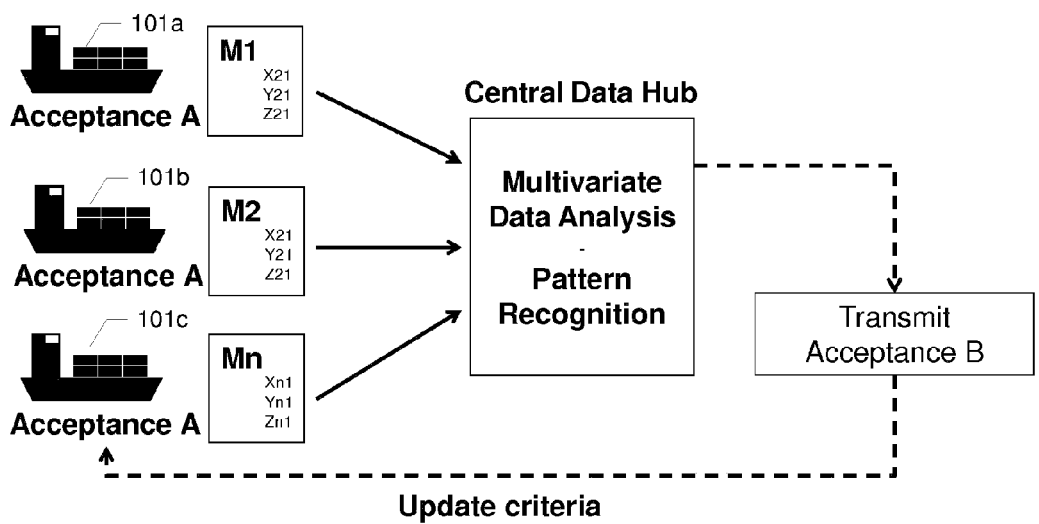
FIG. 7 illustrates schematically the BWMS and an algorithmic enhancement process applied by a data hub computer to ballast water data collected on a plurality of on-board ballast water systems.

The central data hub 103 is configured to store and transmit the set of acceptance criteria to all of the on-board ballast water systems of the same type (or treatment methodology, when comparable). Ballast water treatment systems of the same type are preferably configured to apply the same combinations of ballast water treatment technology to the ballast water. This is schematically illustrated on FIG. 7 where a plurality of ships 1-n includes the same type of ballast water treatment methodology. One exemplary combination of ballast water treatment technology is filter and UV-treatment and another exemplary treatment technology may be hydrocyclone and chlorination etc. The respective ballast water data M1, M2, Mn from the on-board ballast water systems of the ships 1-n are transmitted to the central data hub 103 via the previously discussed bi-directional data communication link. The ballast water data comprise the measured values of the relevant ballast water parameters supplied by the ballast water quality sensor(s). Preferably, the ballast water data also comprise one or more optional ballast water quality parameters, e.g. one or more of temperature, turbidity etc. The ballast water data of each vessel in addition comprises the geographical position of the vessel and possibly other available environmental data of the vessel as mentioned above. The ballast water data of each vessel are preferably structured into a matrix or other suitable pre-defined data format. Each matrix may comprise a plurality of data subsets, where each of these sub-sets contains values of a plurality ballast water quality parameters measured on a ballasting event or de-ballasting event. The sub-sets preferably contain respective values of the plurality ballast water quality parameters before and after a ballast water treatment process. In addition, each of the data matrices preferably includes values of the previously discussed optional ballast water quality parameters. The data matrices are sent to the central data hub 103 where the data hub computer is configured to perform the algorithm enhancement process that preferably comprises multivariate analysis and pattern recognition (e.g. based on PCA) of the uploaded ballast water data/matrices as schematically illustrated on FIG. 7. Patterns and relations in the data subsets of the uploaded matrices are found during the algorithmic enhancement process and utilized to generate the set of acceptance criteria B for the on-board computer of the ballast water system of the specific ship at the known geographic position. As shown in example box 6, the algorithm enhancement process computes an updated set of acceptance criteria, i.e. acceptance criteria B in the present example, for a specific ship's on-board ballast water system. The data hub computer transmits this updated set of acceptance criteria wirelessly back to the on-board computer via the bi-directional data communication link for full or at least partial replacement of the initial set of acceptance criteria A. Obviously, the example given in Box 5 will also be valid when two or more vessels are configured to transmit respective ballast water data to the central data hub 103 for analysis by the algorithmic enhancement process. The computation of the updated set of acceptance criteria will be more comprehensive and accurate when a large of number of vessels participates in the pattern recognition performed by the algorithmic enhancement process in the data hub computer.

As shown in Box 6 the use of ballast water quality data from other BWMS of same type will quickly increase the accumulated amount of uploaded ballast water data from the on-board ballast water systems of the plurality of ships and lead to an improved setting of the set of acceptance criteria transmitted to each of the on-board ballast water monitoring systems in connection with ballasting. Hence, providing a more robust assessment of the ballast water quality and in turn an improved treatment via the updated settings of the values of the acceptance criteria.

---

Box 6. Example of the adjustment of the initial acceptance criteria of the on-board ballast water system based on central hub data analysis.

---

Chlorophyll performance algorithm show poor performance:

f0 = fv/fm > 75

BWMS technology efficacy data (from literature or operator, e.g. for UV technology):

Actual Treatment Dose = Approved Treatment Dose (from Manufacture's Type Approval, typically 140-560 mJ/cm2) * 1/ Turbidity (transmittance)

Approved Treatment Dose * Actual Flow rate/Approved Flow rate = Actual Treatment Dose In example (unit less): 75 = Approved BWMS dosage * $\Sigma$1/BWMS (Turbidity) * $\Sigma$pump rateActual/pump rateApproved

---

An algorithm component of the algorithmic enhancement for the phytoplankton population via chlorophyll a measurement is outlined in box 5. In the BMWS, the results of the measurements of the phytoplankton population are transmitted to the central data hub 103. The pattern recognition analysis may identify that despite very high turbidity or high chlorophyll a concentrations as monitored by the analysis of the data hub computer, no alarms were found. In this situation the central data hub 103 may issue a new set of acceptance criteria for the BMWS on this type of systems that will adjust the original algorithm based on the treatment system's specifications to e.g. allowing an increase of the ballast water quality parameter turbidity from a value of 0.3 units of instead of an initial setting of 0.2 under similar conditions.

Another Example of Adjustment of Algorithm in a BWMS for the Filter Part.

An algorithm for the filter efficacy will originally be based on the treatment system's specifications:

Alarm setting=F(Pore size of filter; efficiency of filter)*k; wherein k a dimension less acceptance criteria related to the environmental conditions and it is typically=1, i.e. there is no adjustment.

Collating and analysing a number of ballasting/de-ballasting events in the central data hub 103 may show that e.g. a number of BWMS alarms occur under low tide conditions. The recognised pattern (i.e. low tides) will lead to an update of settings of the BWMS that will prompt a revised alarm under these conditions:

Alarm setting=$F$(Pore size of filter;efficiency of filter)*$k_x$ where $k_x$ is the updated acceptance criteria related to the geo-position and the tidal conditions. The updated setting of this specific acceptance criterion provides the operator with an early warning if the combination of geo-position and time will result in ballasting under low tide conditions.

Figure 8:
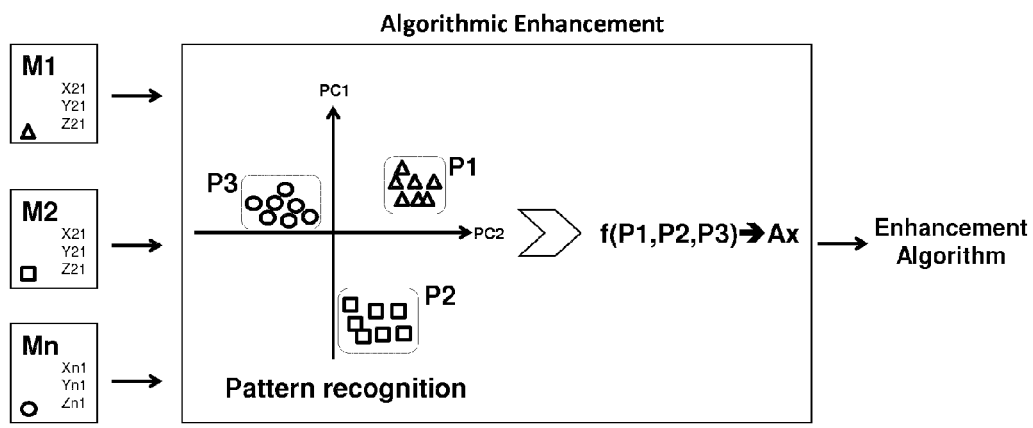
FIG. 8 illustrates schematically how the algorithmic enhancement process executed on the data hub computer determines certain patterns in uploaded ballast water data.

FIG. 8 illustrates schematically how the algorithmic enhancement process executed on the data hub computer determines certain patterns in the uploaded ballast water data M1, M2, Mn from the respective on-board ballast water systems of the plurality of vessels of the BWMS. The algorithmic enhancement process is configured to identify certain correlations or groupings P1, P2 and P3 of co-pending ballast water quality parameters PC1 and PC2. The recognized patterns in variables PC1 and PC2 are used by the algorithmic enhancement process to determine an updated or altered setting of a particular acceptance criterion, or of several acceptance criteria, of one or several corresponding ballast water quality parameter(s). The setting of a particular acceptance criterion may for example be altered to accepting a predetermined increase of the particle concentration in the ballast water, e.g. an increase of 20%, under environmental conditions at the geographic position of the vessel governed by a pattern combining high salinity, low temperature and northern hemisphere winter (i.e. indicating low concentration of phytoplankton and zooplankton).

Figure 9:
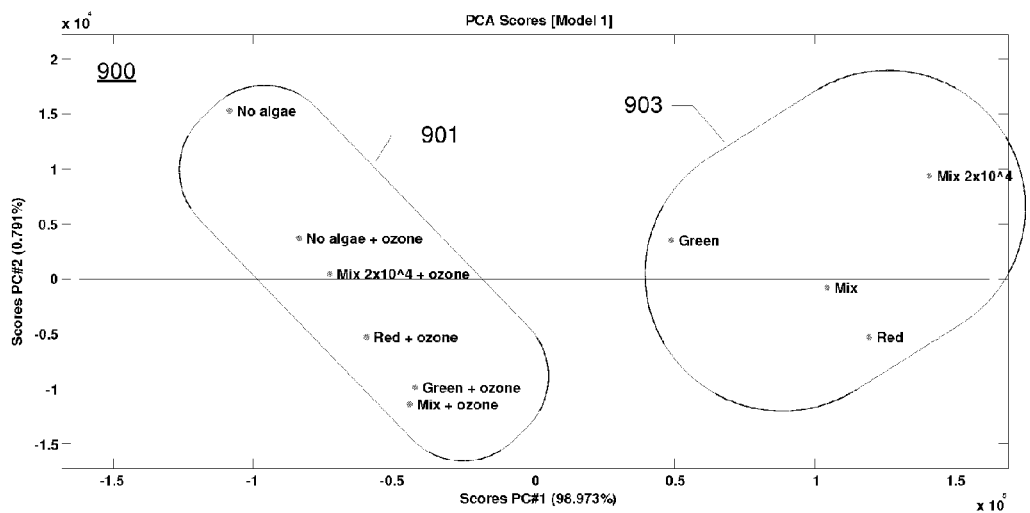
FIG. 9 illustrates results of a principal component analysis of the uploaded ballast water data performed by the algorithmic enhancement process.

FIG. 9 comprises a graph 900 which illustrates results of a principal component analysis of the uploaded sets of ballast water data performed by the algorithmic enhancement process. The x-axis depicts score of the PC#1 and the Y-axis depicts score of PC#2 which provide "explanatory value" of a root cause of variation in the of uploaded sets of ballast water data from the on-board computers of the plurality of vessels of the BWMS. In the present example of principal component analysis, the set of ballast water data in group 901 correspond to treatment of the ballast water and the data set in group 903 correspond to no treatment of the loaded ballast water. With a large number of ballast water datasets this type of principal component analysis is able to provide "explanatory value" or pattern recognition for more subtle root causes and allows for adjustment of the set of acceptance criteria that is transmitted to the on-board computers for monitoring the quality of the loaded ballast water.

Figure 10:
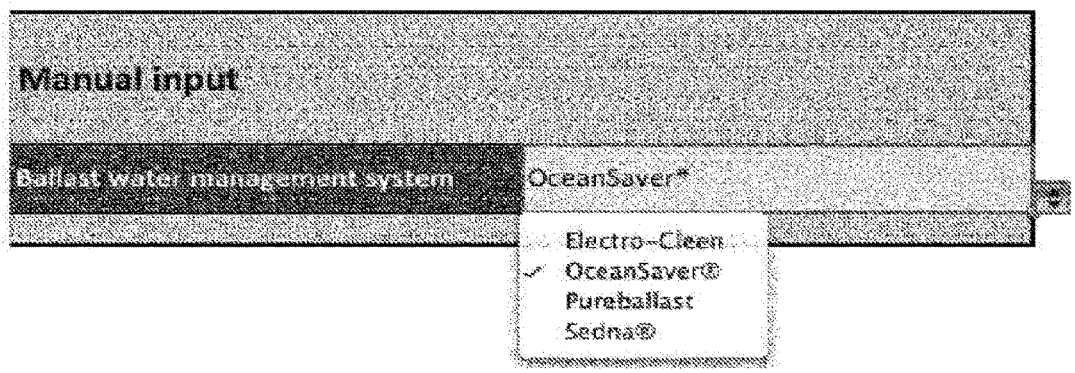
FIG. 10 illustrates an exemplary interface and a pull-down menu of water management system.

FIG. 10 illustrates an exemplary interface and a pull-down menu of the ballast water management system (BWMS) that shows the available choices.

The invention claimed is:

1. A system for monitoring quality of ballast water comprising:
   a central data hub comprising a data hub computer adapted for generating a set of acceptance criteria for ballast water quality parameters at one or more geographic positions based upon uploaded ballast water data from on-board computers of at least two vessels; wherein the uploaded ballast water data indicates where, and when, a volume of ballast water was loaded into a ballast water tank of each of the at least two vessels and the respective values of each of the ballast water quality parameters that are measured on each of the volumes of ballast water; and
   the at least two vessels each comprise an on-board ballast water system comprising:
   an on-board computer with a monitor, a data logger, a data storage for storage of a set of acceptance criteria for a number of the ballast water quality parameters corresponding to a geographical position and at least one geographical position detection means adapted for logging into the data logger the geographical position where the volume of ballast water is loaded into the ballast water tank,
   a number of ballast water quality sensors each being adapted for measuring at least one of the ballast water quality parameters of the ballast water in the ballast water piping or in ballast water tank, and adapted for logging ballast water data comprising a value of each of the ballast water quality parameters into the data logger,
   the on-board computer being further adapted for downloading the set of acceptance criteria from the central data hub and up-loading the ballast water data and the corresponding geographical position to the central data hub,
   wherein the on-board computer is adapted to perform a comparison of the values of the ballast water quality parameters with corresponding acceptance criteria corresponding to said geographical position, and
   to display information on the monitor depending on said comparison; and
   if a result of the comparison indicates non-compliance with the acceptance criteria corresponding to said geographical position;
   discharge uploaded ballast water or subject the uploaded ballast water to a filtering treatment or disinfection treatment using a ballast water treatment device;
   if the result of the comparison indicates compliance with the acceptance criteria corresponding to said geographical position; and
   keeping the ballast water in the ballast water tank.

2. A system for monitoring quality of ballast water according to claim 1, wherein each of the on-board ballast water systems further comprises: a clock adapted for logging a time of the year and/or time of the day into the data logger of when the volume of ballast water was loaded into the ballast water tank.

3. A system for monitoring quality of ballast water according to claim 1 wherein the information displayed on the monitor depending on said comparison comprises an acceptance or non-acceptance of the quality of the ballast water loaded into the ballast water tank.

4. A system for monitoring quality of ballast water according to claim 1, wherein each of the on-board computers is adapted for wireless downloading a second set of acceptance criteria, corresponding to the same geographical position as the set of acceptance criteria, and to replace the set of acceptance criteria with the second set of acceptance criteria.

5. A system for monitoring quality of ballast water according to claim 1, wherein the ballast water quality sensors are adapted for measuring one or more ballast water quality parameters selected from a group consisting of phytoplankton population, zooplankton population, bacterial population, and particle size distribution.

6. A system for monitoring quality of ballast water according to claim 5, wherein the one or more ballast water quality parameters are measured using a measurement technology comprising at least one of fluorescence, light scattering, or Near Infrared (NIR).

7. A system for monitoring quality of ballast water according to claim 5, wherein the ballast water quality sensors are adapted for measuring one or more additional ballast water quality parameters selected from a group consisting of salinity, temperature, and transmittance.

8. A system for monitoring quality of ballast water according to claim 5, comprising two or more ballast water quality sensors adapted for measuring the values of the same ballast water quality parameter; and
wherein the on-board computer of each vessel is adapted for calculating a difference between the values of a specific ballast water quality parameter measured by the two or more different ballast water quality sensors and to compare the calculated difference with an acceptance criteria and to display information on the monitor depending on said comparison.

9. A system for monitoring quality of ballast water according to claim 1, wherein the data hub computer is configured to acquire meteorological data and/or ambient water data at the geographic position of the vessel and generate the set of acceptance criteria for ballast water quality parameters at the geographic position of the vessel based on the meteorological data and/or ambient water data.

10. A system for monitoring quality of ballast water according to claim 6, wherein the on-board ballast water system of each vessel comprises a ballast water treatment device;
where the ballast water treatment device comprises an inlet and an outlet pipe adapted for leading the ballast water to and from the ballast water treatment device, respectively, and where a first of the two different ballast water quality sensors, adapted for measuring the same ballast water quality parameter, is arranged in connection with the inlet pipe and a second ballast water quality sensor, adapted for measuring the same ballast water quality parameter, is arranged in connection with the outlet pipe such that the first and second ballast water quality sensors are measuring the ballast water entering and leaving, respectively, the ballast water treatment device.

11. A system for monitoring quality of ballast water according to claim 1, wherein the on-board ballast water system of each vessel comprises:
a ballast water quality sensor adapted for measuring a ballast water quality parameter,
a ballast water piping system is arranged for exposing the ballast water quality sensor to the ballast water at two different positions of the ballast water piping system;
where the on-board computer is adapted for calculating the difference between values of a specific ballast water quality parameter measured by said ballast water quality sensor at the two different positions and to compare the calculated difference with an acceptance criteria and to display information on the monitor depending on said comparison.

12. A system for monitoring quality of ballast water according to claim 8, wherein the on-board ballast water system of each vessel comprises a ballast water treatment device;
the ballast water treatment device comprises an inlet pipe and an outlet pipe adapted for leading the ballast water to and from the ballast water treatment device, respectively, and where the ballast water quality sensor is connectable to either the inlet or the outlet pipe for measuring the same ballast water quality parameter such that said ballast water quality sensor is able to measure the same ballast water quality parameter on both the ballast water entering and the ballast water leaving the ballast water treatment device.

13. A system for monitoring quality of ballast water according to claim 1, wherein the on-board ballast water system of each vessel comprises at least one ballast water treatment device;
the at least one ballast water treatment device being adapted for treating the ballast water of the ballast water monitoring system in at least two different operating modes, and where the on-board computer is adapted for regulating or switching the ballast water treatment device between the different operating modes depending on said comparison of the values of the ballast water quality parameters with corresponding acceptance criteria.

14. A system for monitoring quality of ballast water according to claim 1, where the on-board computer of each vessel is adapted for wireless uploading of the ballast water data to the central data hub.

15. An on-board ballast water system comprising:
an on-board computer with a monitor, a data logger, a data storage for storage of a set of acceptance criteria for a number of ballast water quality parameters corresponding to a geographical position,
at least one geographical position detection means adapted for logging into the data logger the geographical position where the volume of ballast water is loaded into the ballast water tank,
a number of ballast water quality sensors each being adapted for measuring at least one of the ballast water quality parameter of the ballast water in the ballast water piping or in ballast water tank, and adapted for logging ballast water data comprising a value of each of the ballast water quality parameters into the data logger,
wherein the on-board computer is adapted to perform a comparison of the values of the ballast water quality parameters with corresponding acceptance criteria corresponding to said geographical position, and to display information on the monitor depending on said comparison, and wherein the on-board computer is adapted for downloading of the set of acceptance criteria from a central data hub; and if a result of the comparison indicates non-compliance with the acceptance criteria corresponding to said geographical position;

discharge uploaded ballast water or subject the uploaded ballast water to a filtering treatment or disinfection treatment using a ballast water treatment device;

if the result of the comparison indicates compliance with the acceptance criteria corresponding to said geographical position; and keeping the ballast water in the ballast water tank.

16. A method of monitoring quality of ballast water in a ballast water tank or ballast water piping on-board a vessel, comprising steps of:

recording or entering into a data logger a geographical position where a volume of ballast water was loaded into the ballast water tank; measuring respective values of one or more ballast water quality parameters of the loaded volume of ballast water;

logging the respective measured values of the ballast water quality parameters into the data logger;

downloading a set of acceptance criteria corresponding to the geographical position where the volume of ballast water was loaded from a central data hub and into an on-board computer equipped with a monitor;

comparing the values of the measured ballast water quality parameters in the data logger with the corresponding acceptance criteria corresponding to said geographical position;

displaying information on the monitor depending on said comparison; and if a result of the comparison indicates non-compliance with the acceptance criteria corresponding to said geographical position;

discharge uploaded ballast water or subject the uploaded ballast water to a filtering treatment or disinfection treatment using a ballast water treatment device;

if the result of the comparison indicates compliance with the acceptance criteria corresponding to said geographical position; and keeping the ballast water in the ballast water tank.

17. A method of monitoring quality of ballast water according to claim 16, wherein the filtering treatment or disinfection treatment of the volume of ballast water is carried out during ballasting in order to reduce a content of e.g. native species of aquatic flora and fauna in the ballast water.

18. A method of monitoring quality of ballast water according to claim 17, comprising further steps of:

measuring values of the same ballast water quality parameter during ballasting before and after the filtering treatment or disinfection treatment, calculating a difference between the values of the same ballast water quality parameter, comparing the calculated difference between the same ballast water quality parameter with an acceptance criterion and display information on the monitor of the on-board computer depending on said comparison.

* * * * *